United States Patent [19]
Nilsson

[11] Patent Number: 6,089,518
[45] Date of Patent: Jul. 18, 2000

[54] MOUNTING DEVICE FOR HOSPITAL EQUIPMENT, MEDICAL SUPPORT SERVICE UNIT THEREFOR AND SERVICE MOBILE

[75] Inventor: Agne Nilsson, Limasol, Cyprus

[73] Assignee: Johnson Medical Development PTE Ltd., Slovenia

[21] Appl. No.: 08/836,591

[22] PCT Filed: Nov. 14, 1995

[86] PCT No.: PCT/SE95/01346

§ 371 Date: Jul. 11, 1997

§ 102(e) Date: Jul. 11, 1997

[87] PCT Pub. No.: WO96/15337

PCT Pub. Date: May 23, 1996

[30] Foreign Application Priority Data

| Nov. 15, 1994 | [SE] | Sweden | 9403972 |
| Dec. 14, 1994 | [SE] | Sweden | 9404354 |
| Apr. 24, 1995 | [SE] | Sweden | 9501522 |

[51] Int. Cl.$^7$ ................................................ A47H 1/10
[52] U.S. Cl. .............................. 248/317; 5/658; 248/324; 248/343
[58] Field of Search .................... 248/639, 343, 248/317, 320, 324; 5/600, 658, 905; 211/26, 113

[56] References Cited

U.S. PATENT DOCUMENTS

| 3,164,355 | 1/1965 | Seitz et al. | 248/324 |
| 3,627,250 | 12/1971 | Pegrum | 248/324 |
| 4,673,154 | 6/1987 | Karapita | 248/320 |
| 4,795,122 | 1/1989 | Petre | 248/317 |
| 4,801,815 | 1/1989 | Biette et al. | 307/112 |
| 4,856,741 | 8/1989 | Schaefer | 248/122 |
| 4,993,683 | 2/1991 | Kreuzer | 248/639 |
| 5,026,017 | 6/1991 | Kreuzer | 248/324 |
| 5,108,064 | 4/1992 | Kreuzer | 248/327 |
| 5,455,975 | 10/1995 | Foster | 5/600 |

FOREIGN PATENT DOCUMENTS

| 0 215 212 | 3/1987 | European Pat. Off. . |
| 0 219 274 | 4/1987 | European Pat. Off. . |
| 0 257 299 | 3/1988 | European Pat. Off. . |
| 0 477 551 | 4/1992 | European Pat. Off. . |
| 0 603 093 | 6/1994 | European Pat. Off. . |
| 2 702 140 | 9/1994 | France . |

Primary Examiner—Ramon O. Ramirez
Assistant Examiner—Tan Le
Attorney, Agent, or Firm—Ladas & Parry

[57] ABSTRACT

Supportive structure to be attached to a ceiling of a hospital room for supporting hospital equipment. The supporting structure comprises beams attached to the ceiling and forming a rectangular space. Inside the space, there are non-interchangeable gas connectors attached to a gas supply of the hospital and a gas-tight electric box comprising terminals connected to the electric supply of the hospital. The equipment is mounted on support plates, which in turn are supported by support profiles attached to beams. The equipment is connected to the non-interchangeable gas connectors inside the space. Gas-tight hoses are provided between the electric box and the equipment for enclosing the electric wires between the terminals of the electric box and the equipment. In this way separate gas-tight passages are provided for the electric wires, avoiding hazard risks. The support plates support medical support service units for intensive care rooms forming a support structure for equipment necessary close to the bed in an intensive care room, such as a monitor (90), suction units (97), blood pressure monitors. The service unit is a rectangular frame (85, 86, 87, 88) supported by a pivotable arm (82, 83, 80) and a bearing (84), in order to extend essentially vertically from the arm and downwards to adjacent the floor. The rectangular space is sufficiently open for allowing sight through the frame for supervision of the patient. The space outside the vertical beams is free for service staff to work. The service unit can also be supported by a stand including wheels.

12 Claims, 16 Drawing Sheets

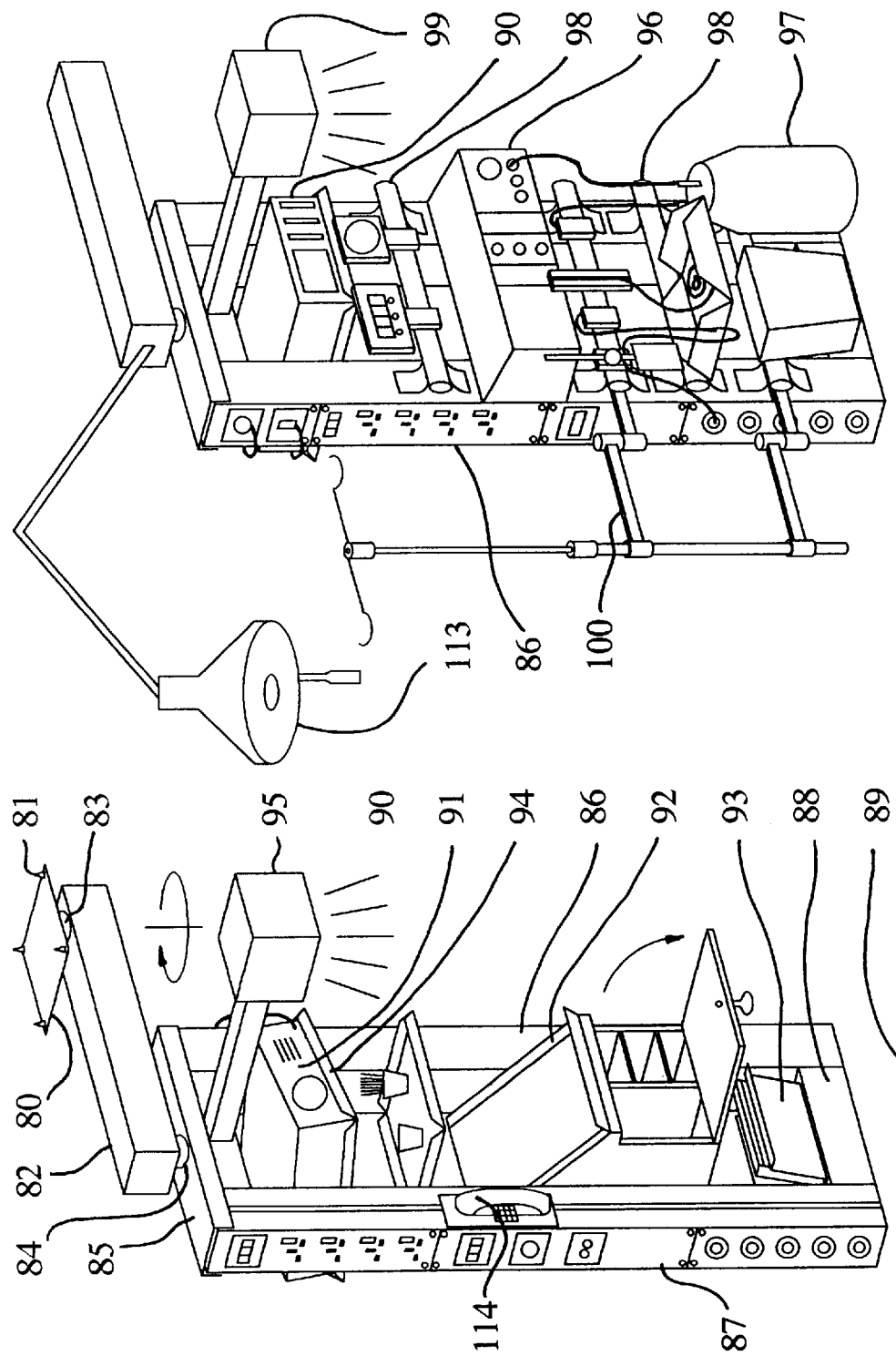

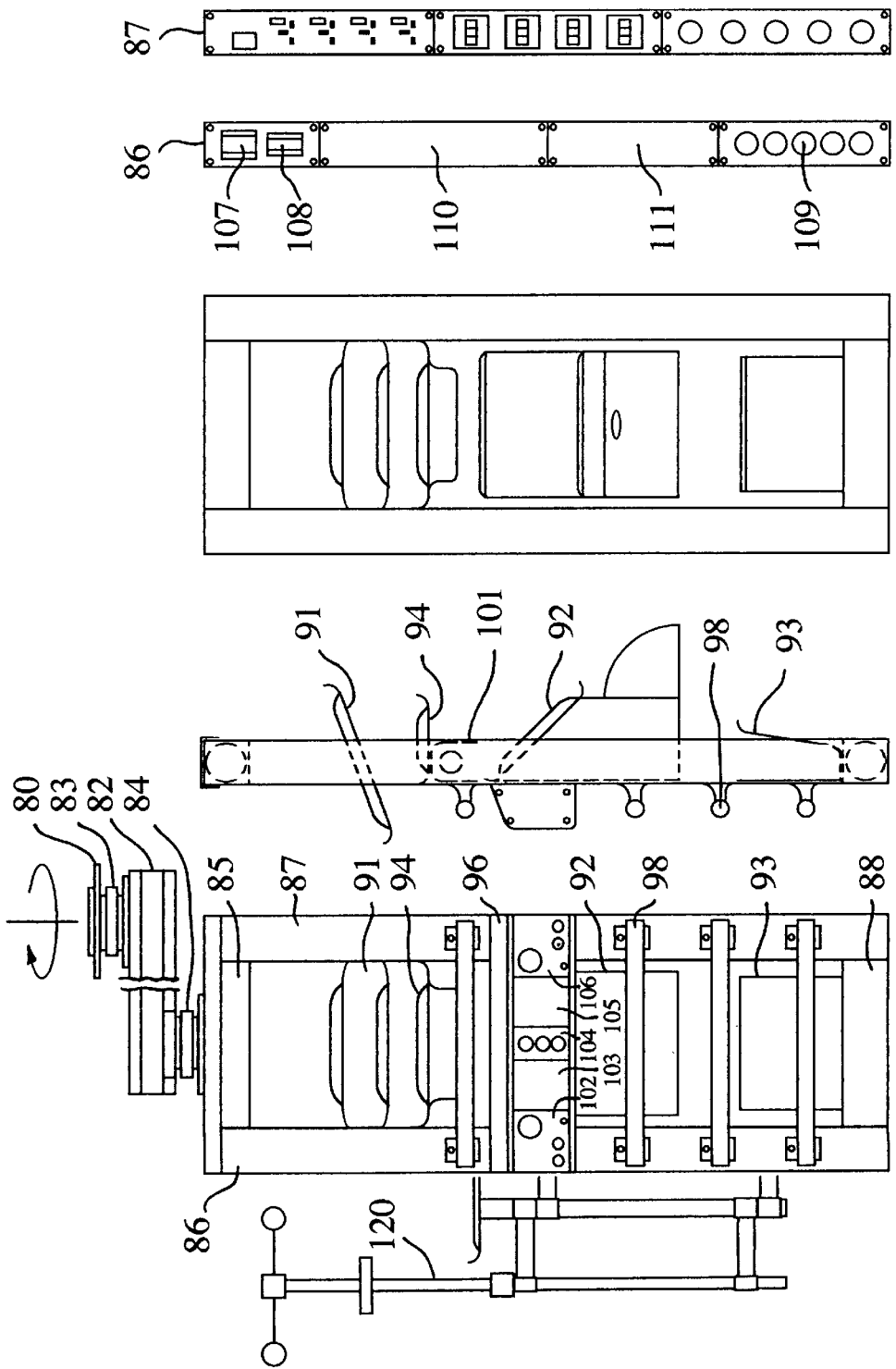

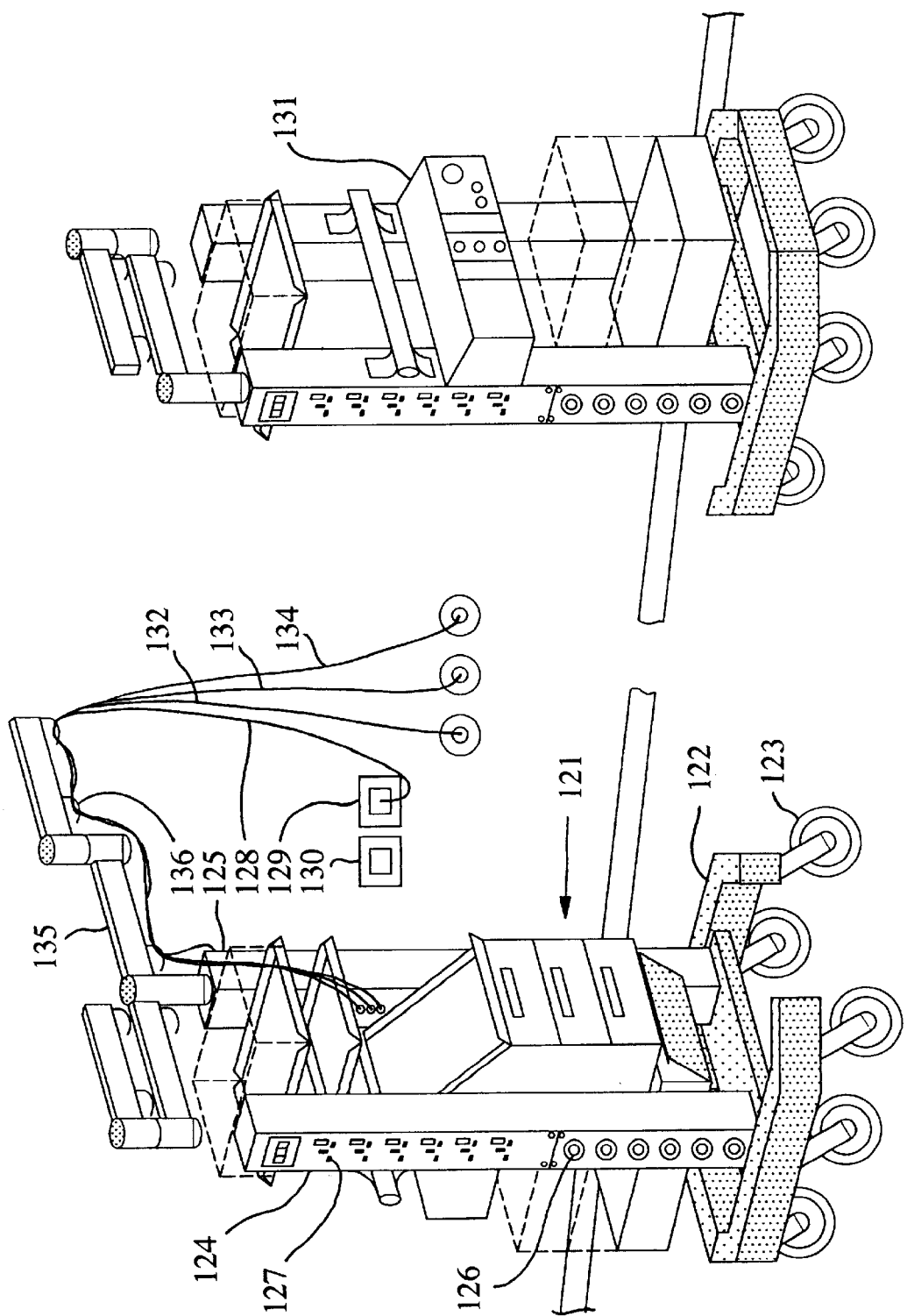

MOUNTING DEVICE FOR HOSPITAL EQUIPMENT, MEDICAL SUPPORT SERVICE UNIT THEREFOR AND SERVICE MOBILE

AREA OF INVENTION

The present invention relates to a mounting device for mounting hospital equipment in the ceiling of a operation room and medical support service unit mounted in said mounting device as well as a service mobil to be used in hospital rooms.

PRIOR ART

A mounting device for mounting equipment in the ceiling of a hospital room is previously known from e.g. EP-A2-0215212. Said mounting device comprises electric wires and/or fluid ducts. Moreover, it includes a support device for medical equipment.

EP-A2-0 257 299 discloses a support arm suspended in the ceiling and for supporting equipment close to a bed at a hospital.

Another support arm system and mounting equipment for a hospital is disclosed in CH-A5-568 459 (corresponding to U.S. Pat. No. 3,931,452).

U.S. Pat. No. 5,108,064 discloses a applicance support for use in particular in intensive care stations and comprising a support arm for receiving support members for the appliances and supply connections for operating the same.

EP-A1-0219 274 discloses a support frame for medical apparatuses to be used close to the bed at a hospital and supported by wheels.

An intravenous infusion device mobile is disclosed in EP-B1-477551. The mobile carries a number of infusion devices necessary for the patient. DE-C1-41 04 814 discloses an intravenous infusion device in more details.

The mounting devices for support close to the ceiling of a hospital room and as disclosed in the prior art have the drawbacks that they do not solve the problem of separating the supply means for gas and electricity, which results in a potential risk.

Moreover, in a hospital room, the equipment to be used at the bed side need to be supported in a convenient and practical way. The prior art support devices have drawbacks as to the practicallity and availability of the electric connectors as well as gas connectors.

Within intensive care there is required many service functions such as: several types of drip and infusion systems for nutrition, liquid balance and drug supply; monitoring systems for various vital systems; respiratory support systems and also complete take-over of respiration.

All the above service must be present since the actual need cannot be pre-planned. It is also required that the personnel can conveniently reach the patient for exchanging drip cannulas, making free the respiratory tracts and even be able to do heart massage.

The necessary equipment has to be supported, either by a ceiling attached support system or by a mobile provided with wheels.

DISCLOSURE OF THE INVENTION

According to the present invention, there is provided a supportive structure intended to be attached to the ceiling of the hospital room for supporting hospital equipment and comprising support beams and profiles enclosing internal gas connections and electric connections. The connections for electricity are separated in a gas tight enclosure preventing any contact with gases, which may leak from the gas suppliers. Thus, a completely safe installation is obtained.

According to the present invention, there is also provided a new medical support service unit for intensive care which is more convenient and less cumbersome than previous systems, and is moveable in relation to the bed and still is sufficiently rigid to support also heavy equipment. Thus, there is provided a medical support service unit for intensive care rooms comprising connectors for gas supply and suction, electric power supply and other electric connectors are required and forming a support structure for equipment necessary close to the bed in an intensive care room, such as a monitor, suction units, gas supply units, blood pressure monitors. According to the invention, the unit comprises a rectangular frame of beams, encircling a rectangular space, said frame being supported by a pivotable arm and a bearing mounted in the ceiling of the room, in order to extend essentially vertical from the arm and downwards to adjacent the floor of said room. The rectangular space encloses equipment which are well protected inside the frame, and said rectangular space is sufficiently open for allowing sight through the frame for supervision of the patient and contact with other staff and the area around the vertical beams being free for service. The vertical beams comprises electric connections and outlets mounted in or at the vertical beams. A gas panel is mounted across the vertical beams.

A further object of the present invention is to provide a mobile where all equipment needed for the intravenous supply services can be included, such as intravenous pumps of the peristaltic or syringe type, nipples, catheters, needles, valves and other small parts, monitors which analyses and monitors the operation of the equipment and the vital functions of the patient. In this way all equipment required for this function can be gathered to one unit. A complete medical support system is obtained for intensive or critical care, which means that the nurses and doctors are given ample place to do their contributions to the care of the patient. The ergonomic and working environmental situation is enhanced, which means that the staff feel more safe and will not be stressed.

Further details appear from the attached patent claims.

SHORT DESCRIPTION OF THE DRAWINGS

Further objects, features and advantages of the present invention will appear from the following detailed description of preferred embodiments shown on the attached drawings.

FIG. 10 is a perspective view similar to FIG. 1 of a preferred embodiment of a service unit according to the invention.

FIG. 11 is a perspective view of the service unit according to FIG. 10 from the other side.

FIG. 12 is a side view of the unit seen from the bedside without any equipment.

FIG. 13 is an end view of the unit according to FIG. 12.

FIG. 14 is a side view of the unit according to FIG. 12 seen from the nurse side.

FIGS. 15 and 16 are elevation views of the side of the vertical beams.

FIG. 18 is a perspective view of a ventilation mobile, seen from the nurse side.

FIG. 19 is a perspective view of the ventilation mobile according to FIG. 18, seen from the patient side.

DETAILED DESCRIPTION OF THE INVENTION

Figure 1:
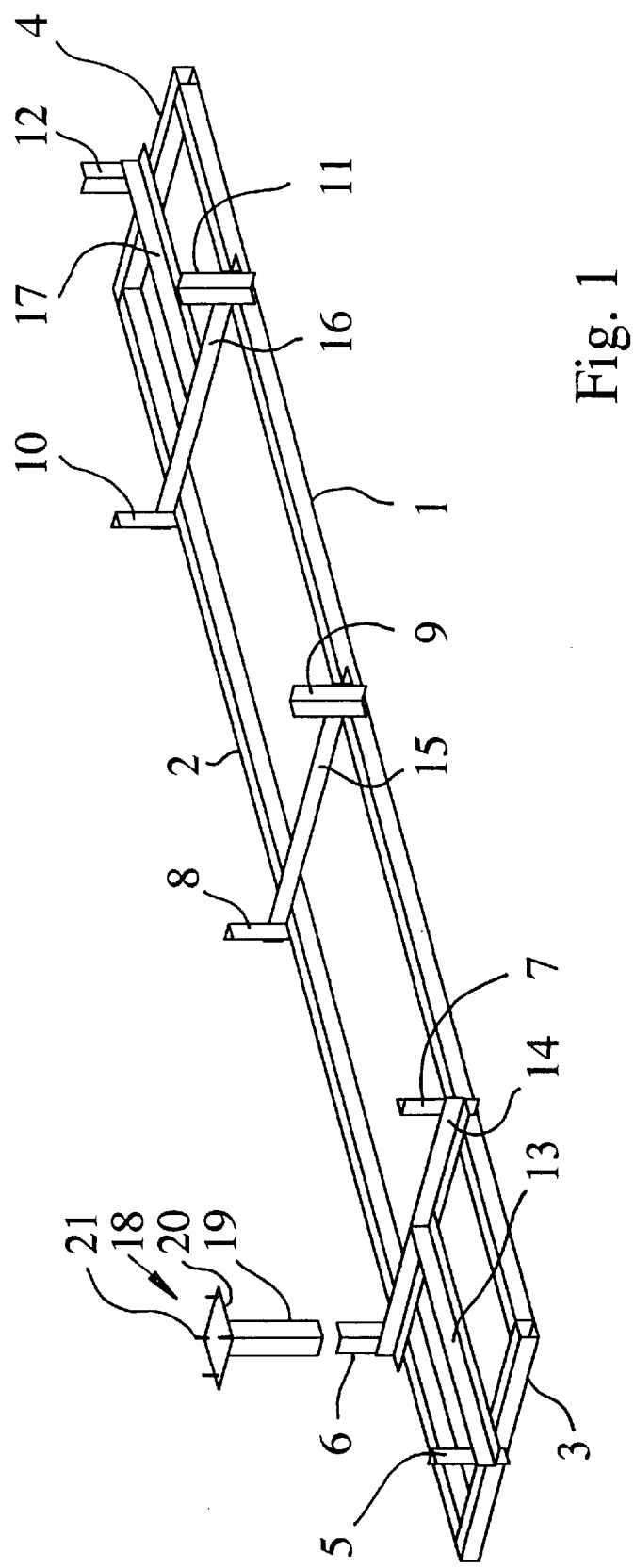
FIG. 1 is a perspective view of a supportive structure according to the invention.

FIG. 1 is a perspective view of the supportive structure comprising steel girders making up the installation.

The supportive structure comprises a rectangular framework of rigid square steel girders. In the drawings there are shown two longitudinal girders 1, 2, each for example 3600 mm long, interconnected by two transversal girders 3, 4 each for example 600 mm long. Several vertical L-beams 5–12 are welded to the square girders at suitable locations as shown on the drawings. Further horizontal L-beams 13–17 interconnect the vertical L-beams to form a supportive structure as shown on the drawing.

Each vertical L-beam is intended to be connected to mounting members 18, one of which is shown on the drawing above L-beam 6. It is to be understood that such mounting members are positioned above each of the vertical L-beams.

The mounting member comprises a vertical, hollow, square beam 19 attached to a support plate 20. The support plate 20 is attached to the ceiling of the operating room by several screws 21, schematically shown on the drawing.

The square beem 19 of the mounting member 18 has an inner dimension suitable for entering the vertical L-beam inside it. As an example, the square beem can have an external size of 50×50 mm, and a wall thickness of about 2 mm, and thus the inside dimension is about 46×46 mm. The L-beam can have a corresponding dimension so that it fits inside the square beam, such as a width of 45 mm.

When mounting the supporting structure in an operating room, the mounting members are attached to the ceiling in appropriate locations. The vertical L-beams 5–12 are introduced into the square beams until the supportive structure is horizontal, and then the L-beams 5–12 are welded to the square beams. In this way it is possible to obtain a horizontal supportive structure also when the ceiling is not completely horizontal or is uneven.

As mentioned above, the supportive structure comprises four girders, such as square girders of steel and having a dimension of 50×50 mm. The girders have to be strong enough for supporting heavy equipment and can be made with a wall thickness of 2.4 mm.

Figure 2:
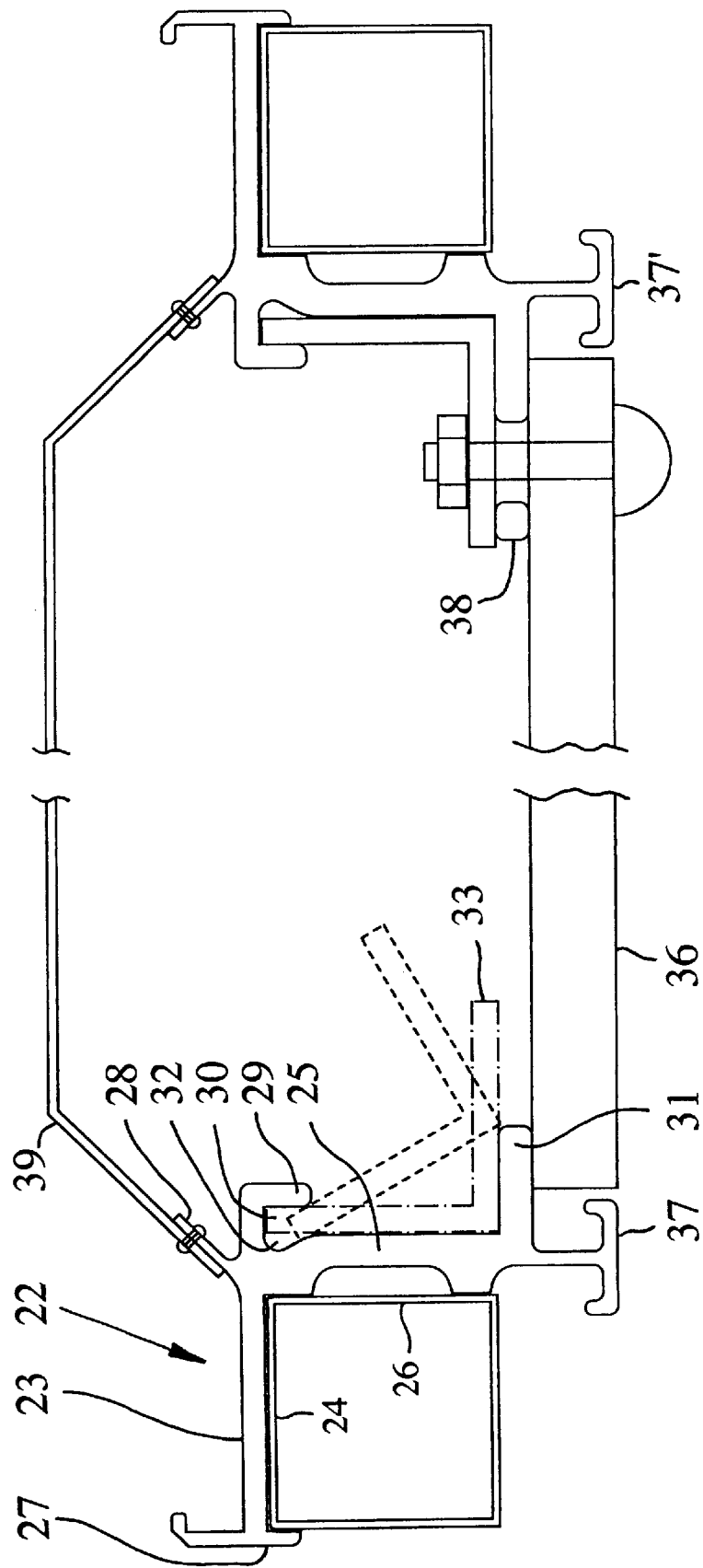
FIG. 2 is an enlarged cross-sectional view of a part of the supportive structure according to the invention.

In order to adapt this supportive structure to support different operating equipment, such as operation lamps, connector centrals for gas supply and electric supplies etc., there is provided according to the invention a support profile made from extruded aluminum having a shape shown in FIG. 2 to the left, and being generally L-shaped. The support profile is intended to be placed along the longitudinal girders. If the support profile is as long as the girder, such as 3600 mm, then the support profile has recesses for passing the vertical L-beams 5–12.

The support profile 22 is shown in more details in FIG. 2 and comprises a first horizontal leg 23 intended to be placed on the horizontal upper surface 24 of the girder, and a vertical leg 25 intended to be placed along the vertical side surface 26 of the girder facing the inside of the rectangular space formed by the supportive structure. The horizontal leg 23 has a hook flange 27 passing a short distance along the opposite vertical side surface of the girder facing outwards. Thus, the support profile is hanged upon the girder by placing the hook flange 27 over the girder and the profile will hang as shown in FIG. 2. The support profile has several other flanges, the operation of which will be described below.

Somewhere along the upper horizontal surface of the support profile, there is a flange 28 inclined about 45° upwards as shown to the left in FIG. 2. This flange is for supporting a ceiling or lid plate 39 extending from one girder to the other and covering the whole supporting structure at the top. Preferably, the ceiling plate 39 is extending inclined upwards about 50 mm and then extends in a horizontal direction. The ceiling plate 39 is attached to the flange 28 by rivets or screws.

The support profile is further provided with a depending flange 29 close to the intersection between the horizontal and vertical legs 23, 25 forming a pocket 30 facing downwards and extending along the entire length of the support profile. Furthermore, the vertical leg 25, at the bottom is provided with a horizontal flange or support surface 31 extending inside the rectangular area of the supportive structure. The object of the pocket 30 and the surface or flange 31 is to support an L-beam, as shown in broken lines in FIG. 2. The pocket 30 is provided with an enlargement 32 enabling the introduction of a L-beam 33 as shown in FIG. 2 by broken lines.

Figure 3:
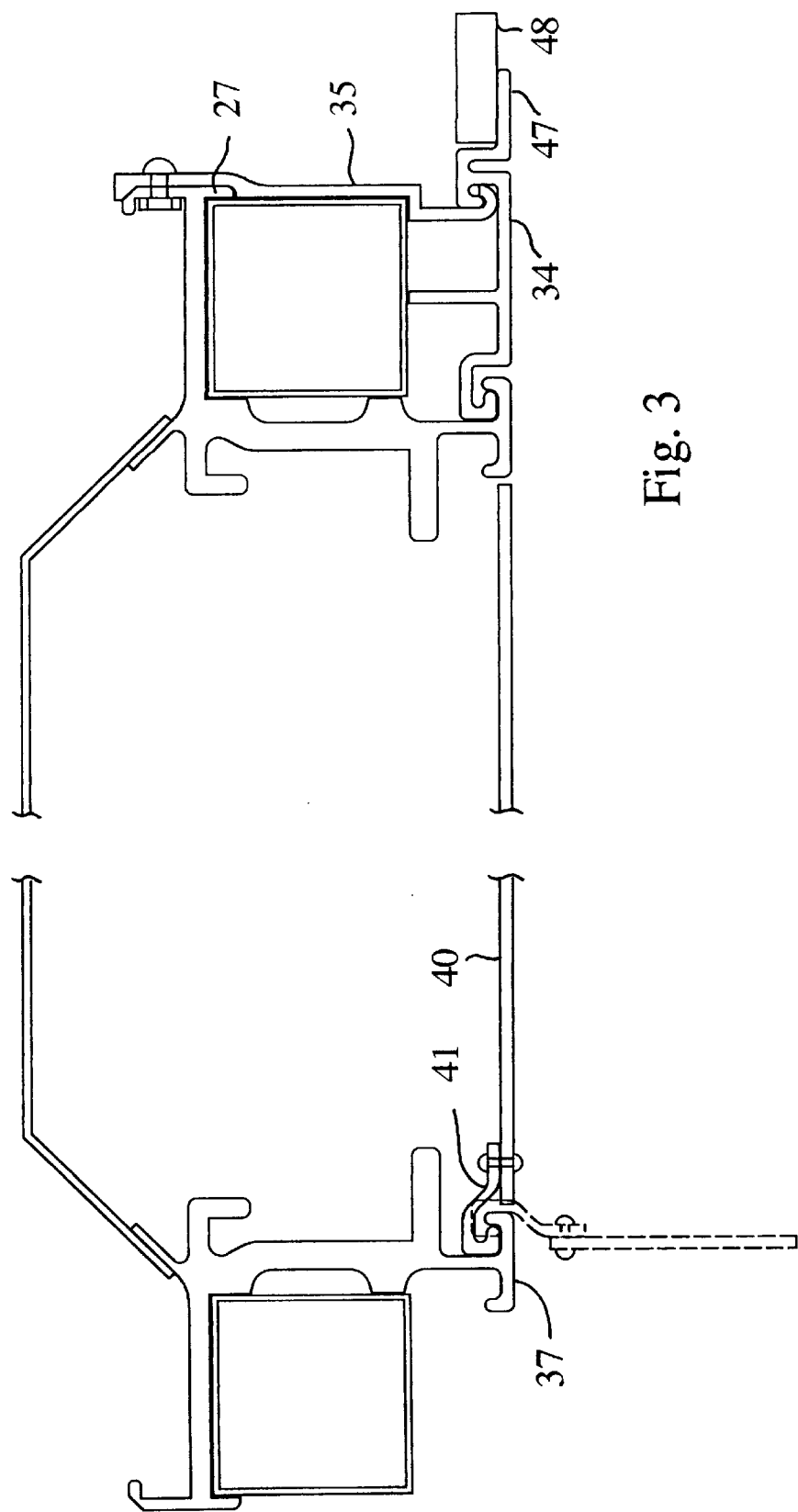
FIG. 3 is an enlarged cross-sectional view of another part of the supportive structure according to the invention.

As shown at the right side of FIG. 3, each girder is provided with a cover profile 34 extending along the entire length of the girder. The cover profile is locked in place by a lock profile 35, which can be placed on intermediate positions or can be a longitudinal profile. The lock profile 35 is screwed to the hook flange 27 of the support profile 22, thus completing the grip around the girder. In this way, a very reliable support profile construction is attached to the girders.

As shown to the left in FIG. 2, a longitudinal L-beam 33 can be inserted with its vertical leg into said pocket 30 and resting upon the support surface 31. The L-beam 33 has three holes along its horizontal leg, into which holes are inserted screws for supporting any equipment to be attached to the supportive structure. Such equipment is mounted on a strong support plate 36 having a standardized size, such as 600×300 mm. The girders are mounted so that the distance between a depending inverted T-flange 37 of one girder to the corresponding T-flange 37' of the other girder is 600 mm. The above-mentioned L-beam 33 has a length of 300 mm. Thus, the support plate 36 for the equipment can be inserted between the T-flanges and attached to the L-beams arranged as described above. By drawing the screws, the L-beam 33 and the support plate 36 will squeeze the support surface 31 therebetween forming a tight attachment between the support plate 36, the L-beam 33 and the support profile 22. Preferably, the L-beam has a cushion 38 outside the holes as shown in FIG. 2, to the right.

By loosening the screws, the support plate will be moveable along the length of the support profiles and thus along the girders, in order to place the equipment where needed. When the right position has been obtained, the screws are tightened. The equipment can be remounted by loosening the screws and removing them completely, whereupon the support plate is free from the L-beams. Mounting and dismounting of the equipment can take place without making or leaving screw holes in the supportive structure.

When the equipment has been mounted as mentioned above, the spaces between the support plates of respective equipment is downwardly covered by lid plates 40, which preferably are of standard size, or can be cut to the desired size. It is preferred to use a modular size, so that the support plates are placed within modules of a width of 300 mm.

The lid plates 40 are shown in more details in FIG. 3 and are provided with hooks 41, hooking around one of the edges of the inverted T-flange 37. The other side interact with the corresponding edge by a locking arrangement such as an excentric lock (not shown). When the lock is disengaged, the lid plate 40 can be swung down hanging in the hooks 41 when access to the interior of the supportive structure is required a shown in broken lines in FIG 3.

Figure 4:
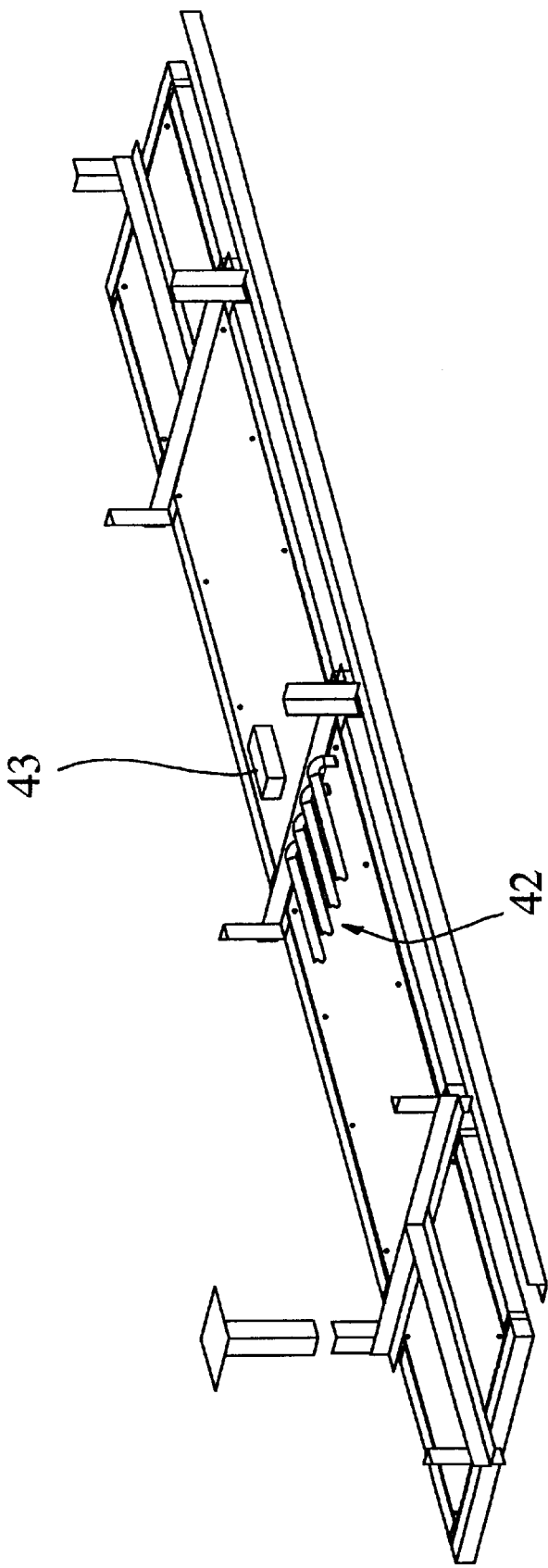
FIG. 4 is a perspective view similar to FIG. 1 and shows the gas conduits.

As shown in FIG. 4, gas conduits 42 are entering the supportive structure from above. Such gas conduits come from the hospital central supply of gas into each room at convenient locations and are connected to non-interchangeable connectors inside the supportive structure. From such connectors, the gas is further supplied to the equipment needing gas supply.

Moreover, electric wires 43 enter the supportive structure from above, as also shown in FIG. 4. These wires enter an electric box 44 (see FIG. 5), provided with suitable terminals. The box is completely gas tight and the holes, through which the wires enter the box are sealed. Thus, there is provided separate and sealed compartments for the electric supply as is required for avoiding risks in connection with gases, such as oxygen gas.

Figure 5:
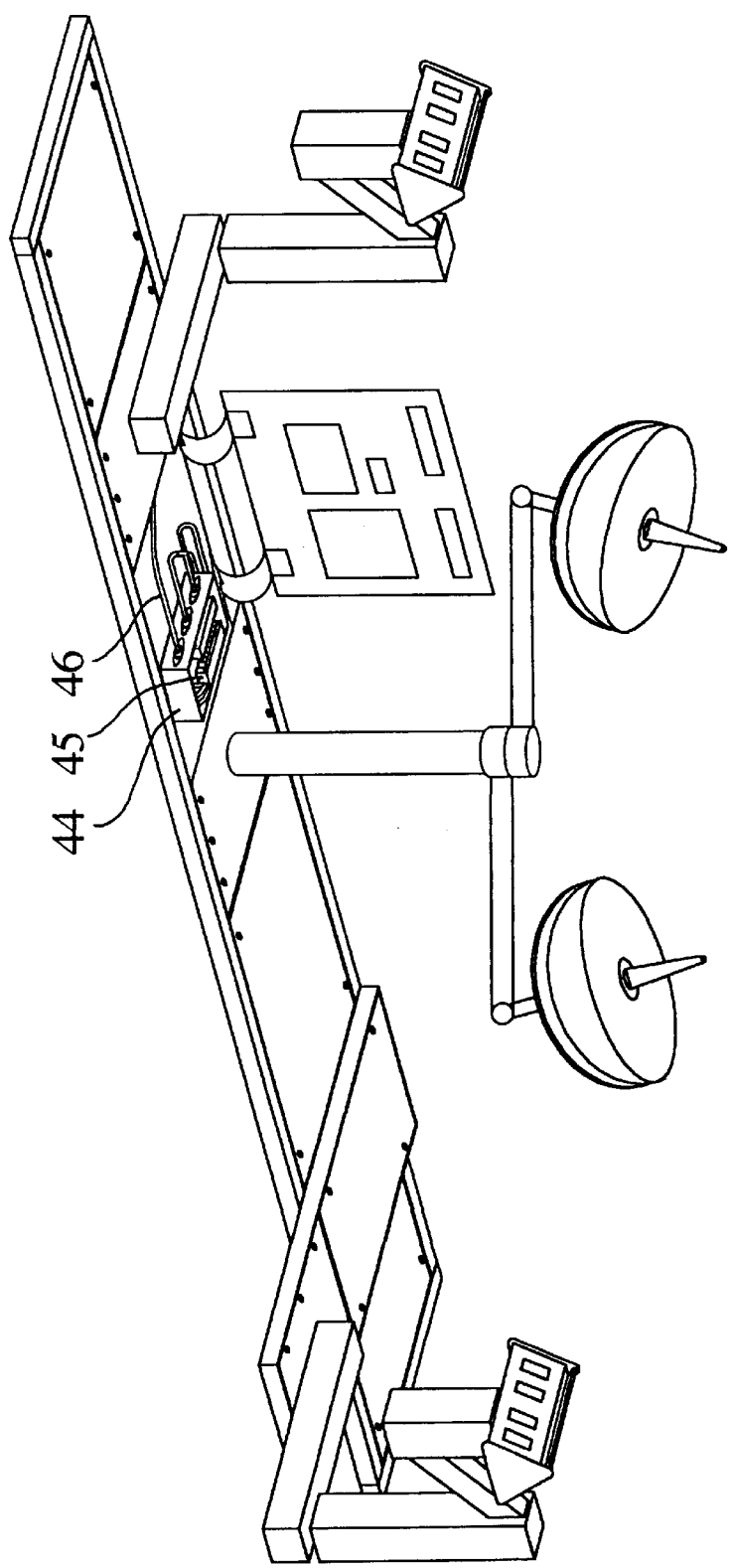
FIG. 5 is a perspective view of the lower side of the supportive structure and shows the electric box.

The electric box has a removeable and sealed cover, which is removed in FIG. 5 exposing the terminals 45 inside the box 44. The electric box is also provided with further holes, which originally are sealed or unbroken. When an equipment needs electric supply, a hose 46 is provided from the electric box to the equipment as shown more clearly in FIG. 6. The hose 46 is gas tightly attached to the electric box by a coupling 47 connected to the box 44 with screws and having a sealing thereto. The other end of the hose is connected to the equipment in a similar way. The electric wires are placed inside said hose and connected to the terminals 45 in the electric box and to the contactors (not shown) of the equipment. Thus, the electric wires are places inside said hose and are sealed from any space that might include gas. Thus, there is obtained a completely safe mounting of electric wires in combination with gas conduits.

Figure 6:
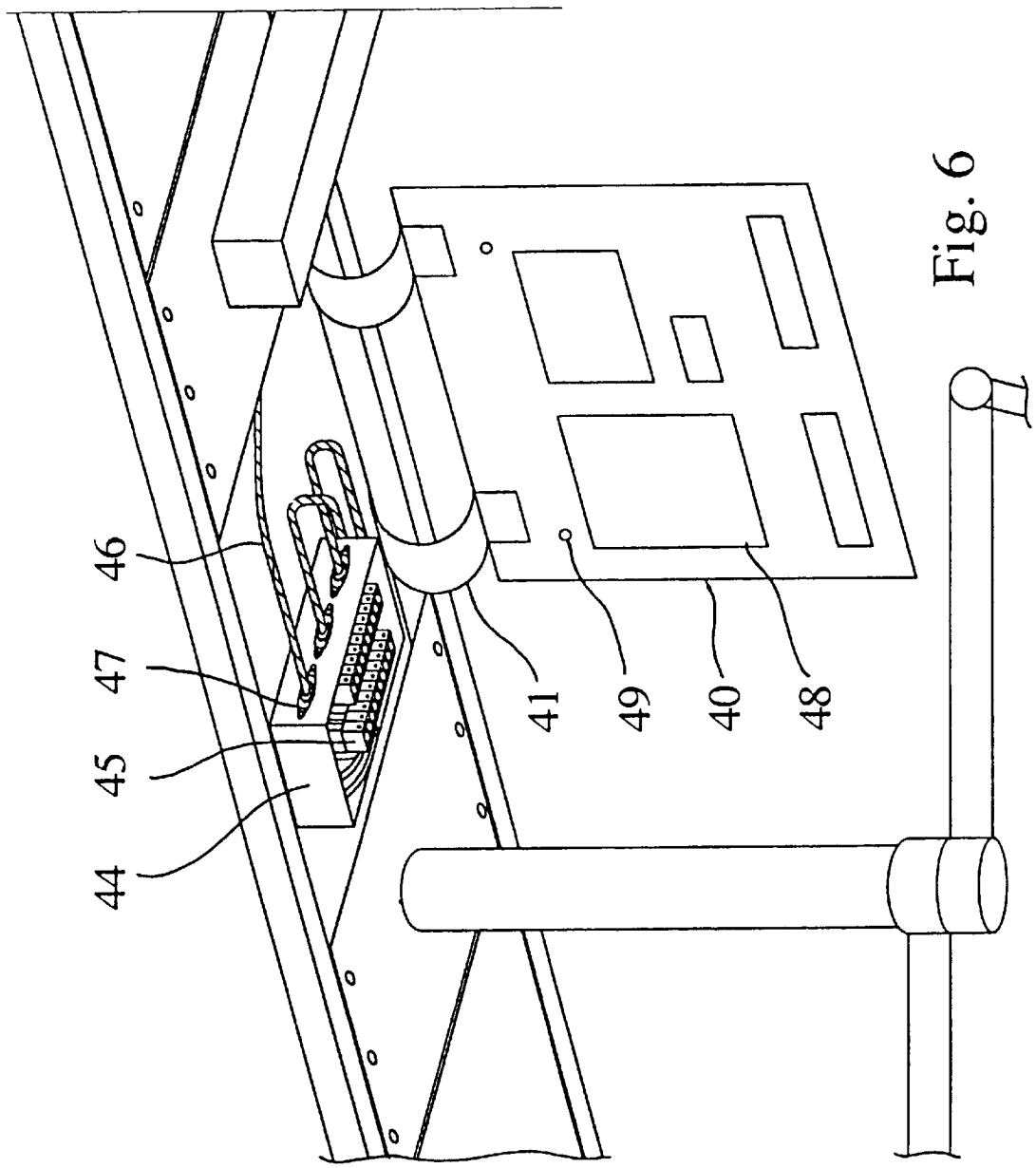
FIG. 6 is a perspective view in an enlarged scale of the electric box according to the invention.

As further shown in FIGS. 5 and 6, the lid plate 40 is shown swung down and hanging in the hooks 41. The inside surface of said lid plate 40 can be provided with circuit diagrams and instruction notes 48 as shown. Moreover, the lid plate is provided with several holes 49. These holes operate as vent holes for venting any gas leaking from the gas non-interchangable couplings to the surroundings. Further such holes 49 are provided in the bottom closures of the supportive structure where necessary.

As shown in FIG. 3, the cover profile 34 is provided with a horizontal flange 47 extending outwards from the space occupied by the supportive structure. This flange 47 is intended to support an extra ceiling 48 of the room, such as a slab, which is often used for obtaining a more clean ceiling surface in the operation room.

It is obvious that the lock profile 35 can be constructed as an integral portion of the cover profile 34 if this is more convenient.

Figure 8:
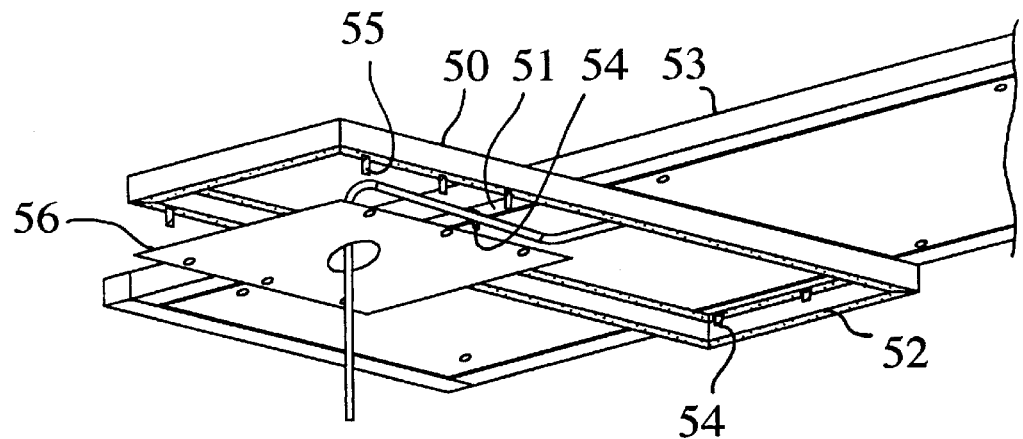
FIG. 8 is an exploded view of the side bracket mounting according to FIG. 7.
Figure 7:
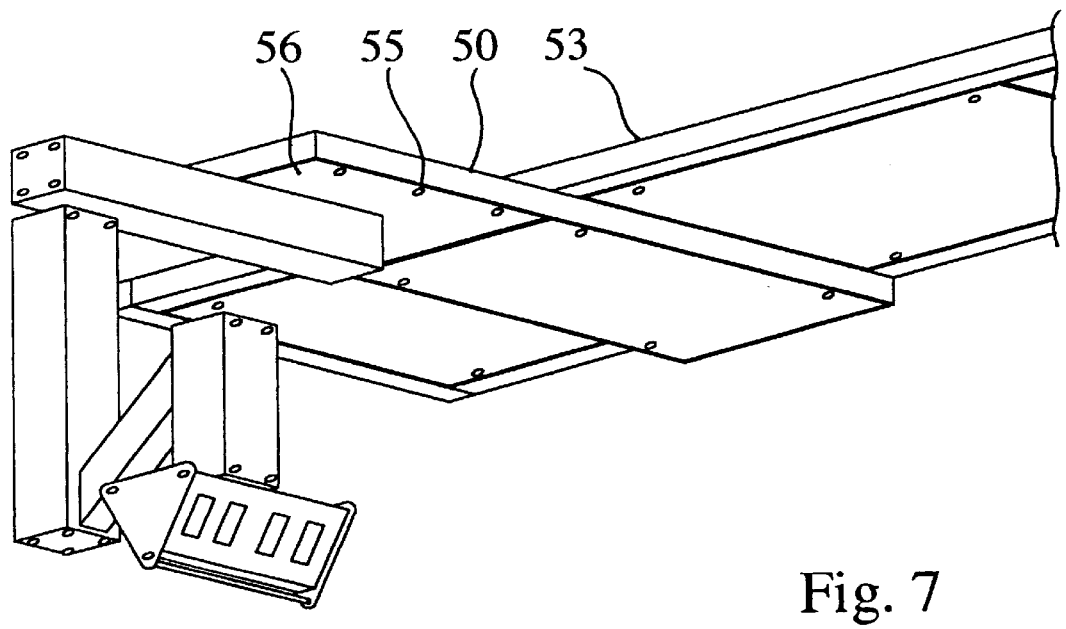
FIG. 7 is a perspective view of an equipment mounted beside the supportive structure in a side bracket.

Sometimes it is desired to place the equipment displaced in the side direction in relation to the supportive structure. Such a bracket mounting is shown in more details in FIGS. 7 and 8. The side bracket is made up of four U-beams forming a rectangular frame 50. The frame is provided with a transversal beam 51. Said beam 51 and one transversal side 52 of said frame are connected to the L-beams 33 as shown in FIG. 2 so that the entire frame 50 is moveable along the supportive structure shown at 53. The frame 50 is locked in position by several screws 54 engaging said L-beams 33 as described above. The frame 50 is provided with screw bolts 55 adapted for engagement with a support plate 56 of the equipment as shown in FIG. 16. The final mounting is shown in FIG. 7.

Figure 9:
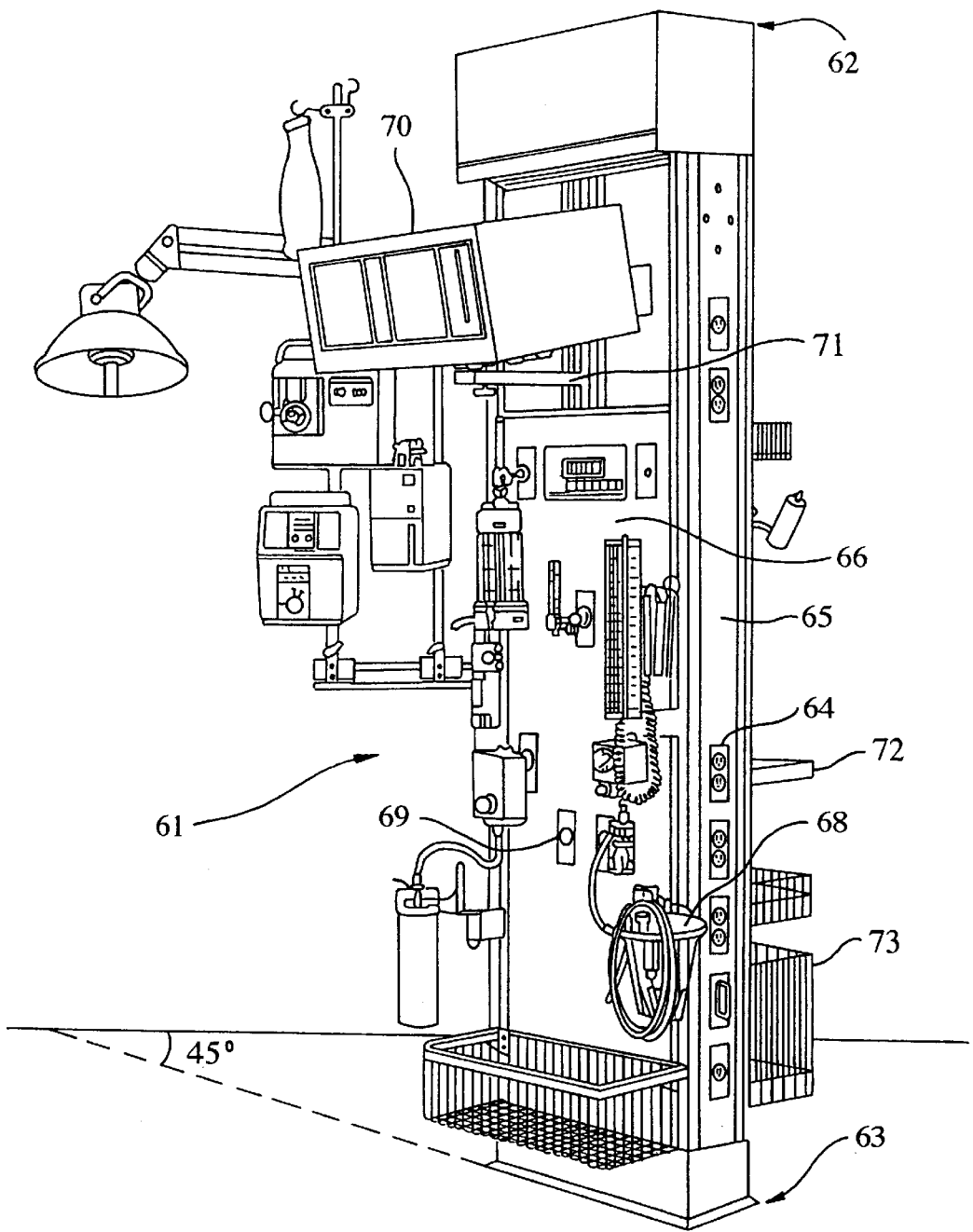
FIG. 9 is a perspective view of a service unit according to prior art.

FIG. 9 is a perspective view of a service unit according to the prior art, the POWER COLUMN from Hill-Rom. It comprises a rectangular column 61 extending from the ceiling 62 to the floor 63 and fixed thereto. The column is about 2400 mm×60 mm×200 mm. The column is mounted about 45° in relation to the adjacent wall. A bed is placed so that the head portion thereof is close to the column. Usually, the bed extends perpendicular to the wall.

The column is provided with several electric outlets 64 and connectors along the vertical short sides 65. Along the long side 66 facing the bed, there is mounted equipment of different types, such as suction devices 69, gas outlets 68. Moreover, a monitor 70 is mounted at a support 71. On the backside there is mounted a shelf 72, where the nurse can write on the patient card, and several boxes 73 for different purposes such as including small details used at the place and a waste basket.

There are several drawbacks with such a service column. It is fixed at the floor which makes it necessary to move the bed, if access to the bed should be required from all four sides in an emergency situation. It happens sometimes that the weight of the patient is monitored by weighting units between the bed and the floor, and a movement of the bed disturbs such a set-up and requires re-calibration of the weighting units.

Since the column is fixed to the floor, it is difficult to clean around the column.

The equipment, and specifically the monitor extends rather long out from the column, which takes up a lot of place. When the nurse makes her patient records, she is positioned behind the column and cannot see the patient, if an emergency situation should arise.

If new equipment is to be mounted, such as a further suction outlet, it is necessary to make new holes in the column construction which is difficult and disturbs other intensive care patients and functions.

A service unit for an intensive care room obviating all the above-mentioned drawbacks with the fixedly mounted column, is shown in FIGS. 10 and 11.

The service unit according to the invention hangs in a support arm supported from the ceiling of the room. Such support arms are frequently used in hospitals, especially in operating rooms.

A support late 80 is attached to the ceiling fixture by several bolts 81. To the support plate 80 is attached a support arm 82 extending horizontally below the ceiling and being pivotable by bearings 83. At the end of the arm, there are further bearings 84 attached to the middle of a horizontally extending beam 85. At the end of beam 85, two vertical beams 86, 87 and 88 form a rectangular frame as shown in FIGS. 10 and 11. The rectangular frame is supported at its vertical symmetry axis by said bearing 84. The bottom beam 88 is placed a short distance above the floor, such as 30 cm above the floor for the necessary convenient cleaning of the floor.

The support plate is attached in the room so that the rectangular frame can be positioned close to the wall in a first position when not used and swung out close to the head end of an adjacent bed when used. The rectangular frame is pivotable around its vertical symmetry axis as shown by arrow 89.

The equipment which must be present close to the bed is mounted in the free space between the vertical beams 86 and 87, as shown by monitor 90 mounted on a shelf 91. The equipment is inserted between the vertical beams and facing the bed side.

On the backside shown in FIG. 10, there is inserted between the vertical beams other types of equipment necessary for the nurse, such as a writing table 92 or commode for the nurse where she can have the patient record and further things for writing purposes. The commode may comprise small boxes containing needles, connector and other accessories for drip, drainage etc.

Alternatively, the commode can be replaced by a PC-station connected to a centralised patient monitoring and recording system, including a video display and keyboard.

At the bottom there is a file box 93. Above the table 92 there is a further shelf 94 for placing stationery, scalpels and other small things handy when arranging for drips etc. A lamp 95 provides a good working light.

It is clear from FIGS. 10 and 11 that a nurse doing her patient records can still observe the patient, through the free space in the interior of the rectangular frame. Only the vertical beams occlude the sight.

At the side usually facing the bed and shown in FIG. 11 there is provided all equipment needed for the patient, such as the monitor 90 mentioned above, a gas panel 96 having gas inlets and a connector for suction connected to a suction collector bottle 97. Several horizontal support rails 98 extend between the vertical beams for supporting further equipment, such as an oxygen therapy unit, timers in case of heart arrest, etc. A lamp 99 provides convenient lighting to the support service system equipment arranged on the unit. The lamp has an oval light up area only to light up the equipment.

A support stand 100 for infusion bags can be attached to the vertical beams as explained in more details below.

The service unit according to FIGS. 10 and 11 is shown without equipment and in side and end views in FIGS. 12, 13 and 14. The same details as in FIGS. 10 and 11 have the same reference numerals.

In FIG. 13 there is shown a different type of lamp 101 included below the shelf 94.

As appears clearly from FIG. 12, the gas panel 96 is provided with several modules 102, 103, 104, 105 and 106. Modules 103 and 105 are blank modules without anything mounted. Module 104 comprises three medical gas pressure indicators showing bright red warning colour when pressure is too low from the central supply, such as oxygen, nitrous oxide and compressed air. To the left, 102 and to the right 106 are two modules having suction units. Other modules can be mounted at positions 103 and 105 without any mechanical work.

The gas panel is connected to the hospital's central gas supply via flexible hoses inside beam 86, beam 85, through bearing 84, arm 82, bearing 83 and support plate 80.

At the sides of the vertical beams 86 and 87 there are several connectors for electric power supply and for signal lines. Thus, the left beam 86, seen according to FIG. 12 is provided with the connectors shown in FIG. 15. Such connectors are power supply outlet 107 and small signal connector 108 intended for the monitor 90. Thus, the wires to the monitor are short. At the bottom there are shown five outlets 109 for power supply (200 V). In between there are two blank modules 110, 111, but these modules can be provided with electric outlets and connectors if required. Other module configurations can easily be arranged.

The corresponding right beam 87 is provided with other connectors as required and shown in FIG. 16. The electric power supply wires and signal wires are enclosed inside the vertical beams 86 and 87 and pass to the hospital's central supply and network the same way as the gas lines.

Thus, it is clear that the rectangular frame can include all functions and equipment necessary for the service function intended. It is easy to adapt the rectangular frame to whatever need should there be.

Since the interior of the rectangular frame is available, compared to the column shown in FIG. 9, the large equipment such as the monitor etc. can be housed between the vertical beams 86, 87 so that they do not occupy large area and do not extend far away from the frame. Such equipment will be positioned below the support bearing 84, and thus, the rectangular frame will be steadily supported by the bearing 84. The equipment will not tend to twist the frame. Thus, a stable service unit is obtained in spite of the fact that it is moveable, which makes it easy to clean the floor. Such equipment is inserted inside the space limited by the vertical beams interleaved from one side or the other. The area outside the vertical beams is free for the support service and comprises the outlets necessary for the service, such as gas outlets and electric outlets.

It is noted that the bearings 83, 84 are of a type allowing very limited movement but rotation around the vertical axis of the bearing. Thus, the rectangular frame is rather rigid and do not move easily, unless movement is wanted. Since all equipment is rather central in the frame, it will be still further stable.

The stability can be further improved by adding a lock in the bearing so that they are locked in position as soon as the frame has been moved into place. Such lock can be a friction clutch or key locking. The lock can be operated by hand, via a wire that can be pulled by hand, or be electrically and/or magnetically operated. Such lock can be included in one or both of the bearings 83, 84.

Moreover, the space between the vertical beams is free so that the patient can be observed even if the personnel is behind the service unit.

Figure 17:
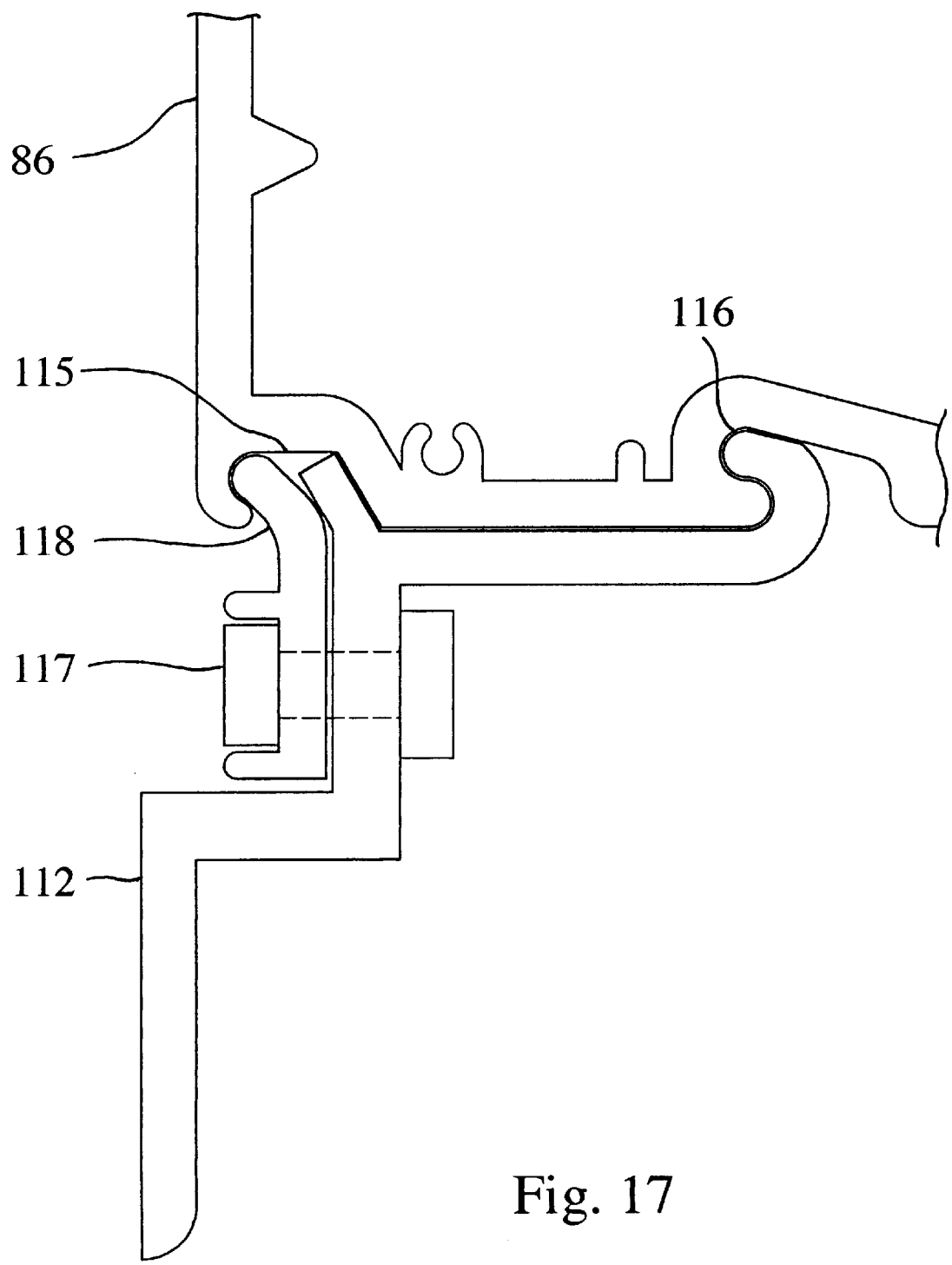
FIG. 17 is a cross-sectional view of a vertical beam with a bracket mounted thereon.

In FIG. 17 there is shown a cross-section through a corner of the vertical beams 86, 87. The beam is provided with vertical grooves 115, 116 in which a bracket 112 can engage. To the bracket 112 can be attached further equipment such as a holder 100 for infusion bags etc. The bracket 112 is locked to the beam by a latch 118 and a screw connection 117 as shown. Other types of equipment can also be attached in this manner.

In FIG. 11 there is shown a treatment lamp 113 attached to the end of the pivotable arm 82. This lamp will be relatively fixed even when the rectangular frame is pivoted around the axis of bearing 84. Thus, said lamp 113 can conveniently be used for illuminating the patient being treated with a constant light, moreover, in FIG. 10 there is shown a telephone 114 in a convenient place. It is easy to install telephone lines in the rectangular frame or the beams.

Critical care of today manage to handle more and more severely ill patients, due to the high capacity of the technique of today in combination with specially educated doctors and nurses. However, this make it necessary to use a great number of different equipment around the patient. In addition to equipment analysing and monitoring the patient, he also requires supply of a lot of nutrients, blood plasma, different anaesthesia etc. Such supply must be controlled which means that old-fashion drop controlled infusion cannot be used any longer and are replaced with electronically controlled infusion pumps and syringes. Up to sixteen such pumps can be used at the same time for a single patient. One common way of using such automatic pumps today is to attach such a pump to the infusion stand with a coupling. The pump is provided with electric power via a wire and is connected to supervisory equipment via a signal cable. It is realised that such a system will be a mess of wires and hoses if used for sixteen pumps. The environment in such critical care rooms can be stressing for the nurses leading to errors and mistakes. It is necessary to further structure and integrate the different functions at such a critical care room.

FIG. 17 shows a ventilation mobile including equipment necessary for respiratory support and for keeping the respiratory ways free, such as oxygen supply units and suction units, as well as further equipment necessary for the critical care, such as supplies for anaesthesia gases. The ventilation mobile is supported by several swivel wheels.

The ventilation mobile 121 comprises a bottom frame 122 supported by several wheels 123 to form a transportable unit. Two vertical pillars 124, 125 extend from the bottom frame to define a vertical rectangular space. Each vertical pillar comprises several outlets for electric power supply 127 and medical gas outlets 126. All power outlets are supplied with 200 V mains power by a power wire 128 connected to a power outlet 129 at the wall of the room and the signal outlets are connected to a corresponding wall mounted signal connector 130, if used (no wire shown in FIG. 17). Moreover, the mobile is provided with a suction unit panel 131 connected to the hospital's central supply of gas via lines or hoses 132, 133, 134. As shown, power wire 128 and hoses 132, 133, 134 are supported by a pivotable arm 135 having hooks 136 supporting said wire and hoses. In this way the pivotable arm 135 can be made smaller and cheaper, compared to if the arm should enclose the hoses.

The vertical pillars 124, 125 and the bottom frame 122 form a vertical rectangular space inside which equipment can be mounted without extending into the space needed for the treatment of the patient. Thus, a large monitor is shown at the top on a shelf, which can be inclined. Moreover, the pillars encloses a writing table facing away from the bed, where the nurse can make the necessary recording and still observe the patient through the open space between the pillars.

As shown in broken lines in FIG. 19, the mobile can be provided with the equipment desired for a specific patient, such as a ventilator supported by said mobile bottom frame 122.

Figure 21:
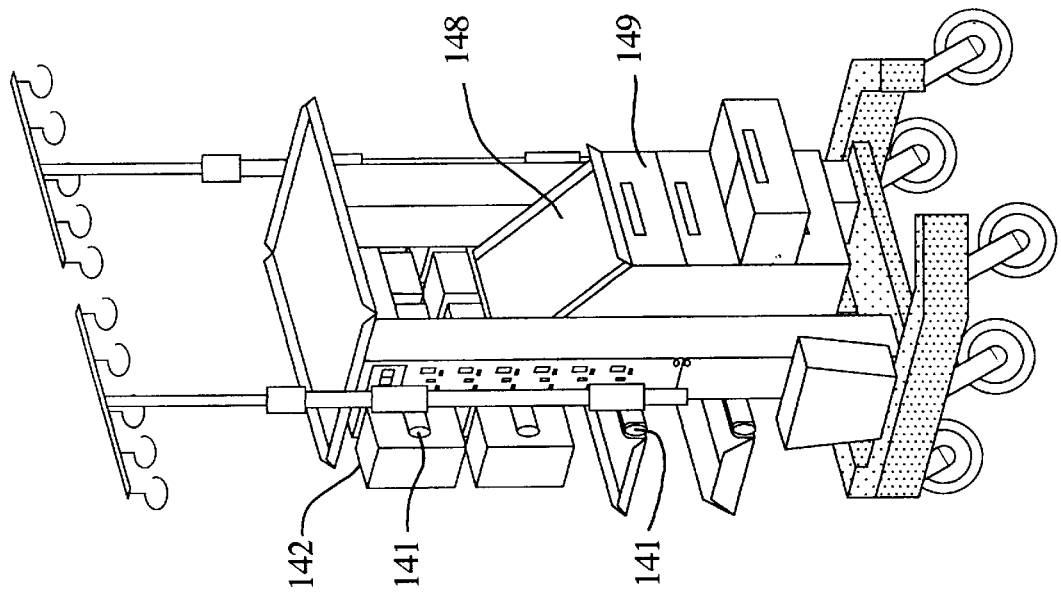
FIG. 21 is a perspective view of the critical care mobile according to FIG. 20, seen from the opposite side compared to FIG. 3.
Figure 20:
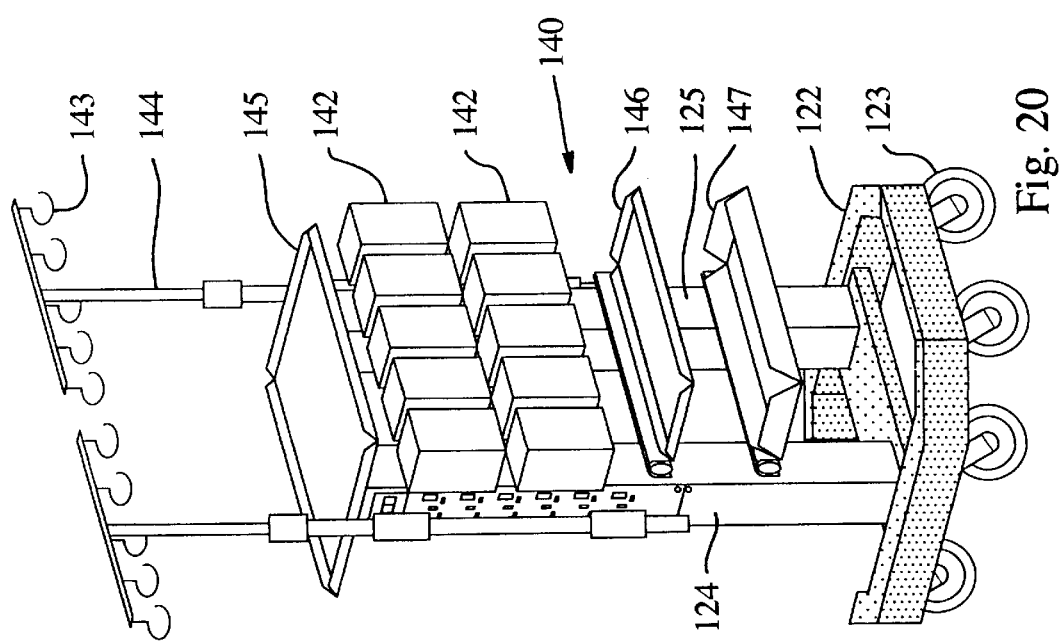
FIG. 20 is a perspective view of a critical care mobile according to the invention, seen from the patient side.

As further shown in FIGS. 20 and 21, the same mobile can instead be constructed as an intravenous mobile or critical care mobile 140. In this case it is not necessary to have gas supplies from the hospital's central supply, but the mobile is only connected to 200 V by a power wire (not shown). The mobile can also be connected to the hospital's central computer system in order to take advantage of the computerised patient recording system used at many hospitals today. Such wires are connected to wall mounted outlet sockets.

As appears from FIGS. 20 and 21, the critical car mobile has the same bottom frame 122, wheels 123 and vertical pillars 124, 125. The side of the mobile facing the bed is provided with several mounting rails, for example four rails 141 as shown in FIG. 21. On said rails 141 are mounted several infusion pumps represented by rectangular boxes 142 if FIG. 20. Said infusion pumps can be of the peristaltic type providing infusion solutions from infusion bags hanging on hooks 143 of a stand 144. There are two such stands 144, one at each pillar, each stand being provided with five hooks. The infusion pumps can also be of the syringe type providing a beneficial agent to the patient, such as antibiotics, insulin etc.

The CC (critical care) mobile 140 is furthermore provided with a shelf 145 bridging the two pillars 124, 125 at the upper end thereof. The shelf 145 can support a monitor (not shown) or whatever is needed in the specific circumstance, such as fluid balance monitors and other analysis and monitoring equipment. Two of the rails support infusion pumps 142. The two bottom rails 141 support one shelf 146, which can be used for syringe pumps and a second shelf 147 which can be used for accessories, such as needles, catheters, etc. If more infusion or syringe pumps are needed, such pumps can replace on or both of said shelves 146, 147.

At the side opposite the patient, the CC mobile 140 is provided with a writing table 148 and a few drawers 149 for enclosing accessories at a convenient position for the nurse.

The pillars 124, 125 of the CC mobile 140 are provided with outlet sockets for providing electric power and signal wires to the pumps etc. of the mobile.

Figure 22:
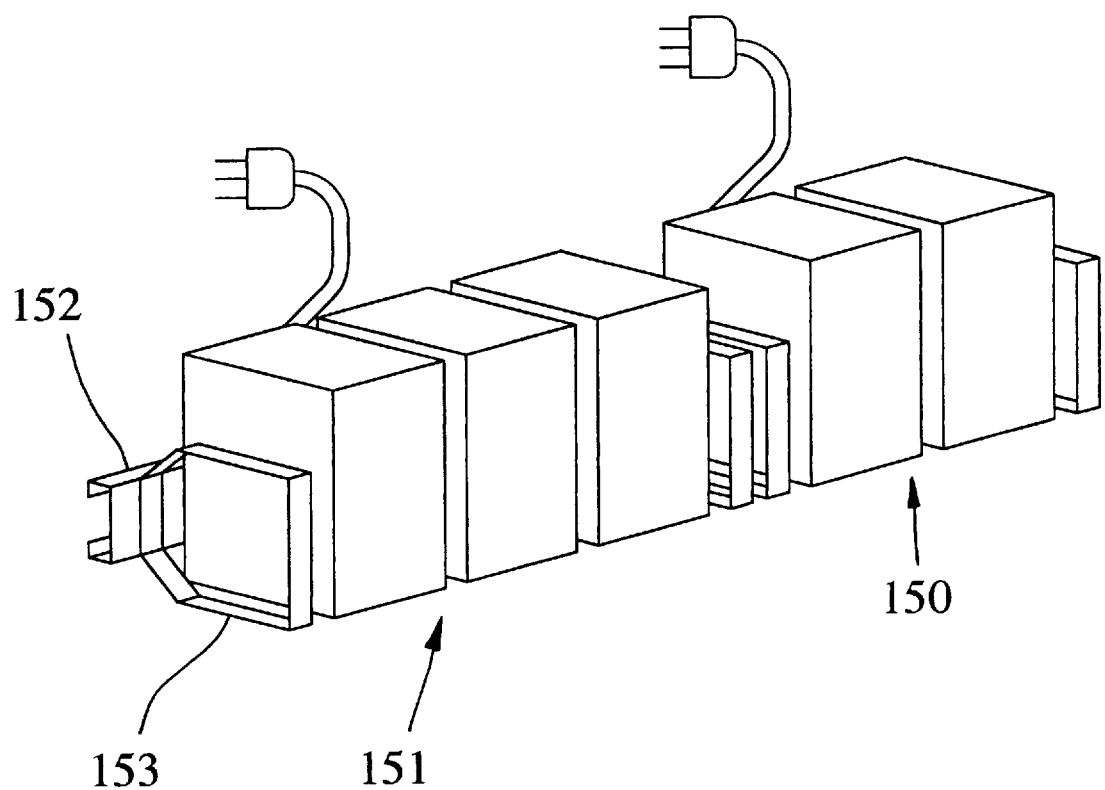
FIG. 22 is a perspective view of a pump module intended to be attached to the mobile according to FIGS. 20 and 21.

FIG. 22 shows the infusion pump sets in more details regarding the attachment to the rails 141. The infusion pumps are mounted in modules, for example a module 150 of two infusion pumps or a module 151 of three infusion pumps as shown in FIG. 22. Each module 150, 151 is interconnected so that only one power wire and one signal wire are needed for each module. The module comprises a holder 152, which in principle is a spring loaded hook grasping around the support rail 141 when brought into engagement therewith.

Each module is provided with handles 153 for easy mounting and dismounting. The modules are stored in the hospital equipment store and when needed taken out and hooked on the support rail. As many pumps as required are mounted and used. By such a module system, it is possible to adapt each mobile to the requirements of each patient. Each module is provided with some co-operating means for engagement with the respective infusion pump. In this way, pumps of different manufacturers can be mounted together if that is desired.

Figure 24:
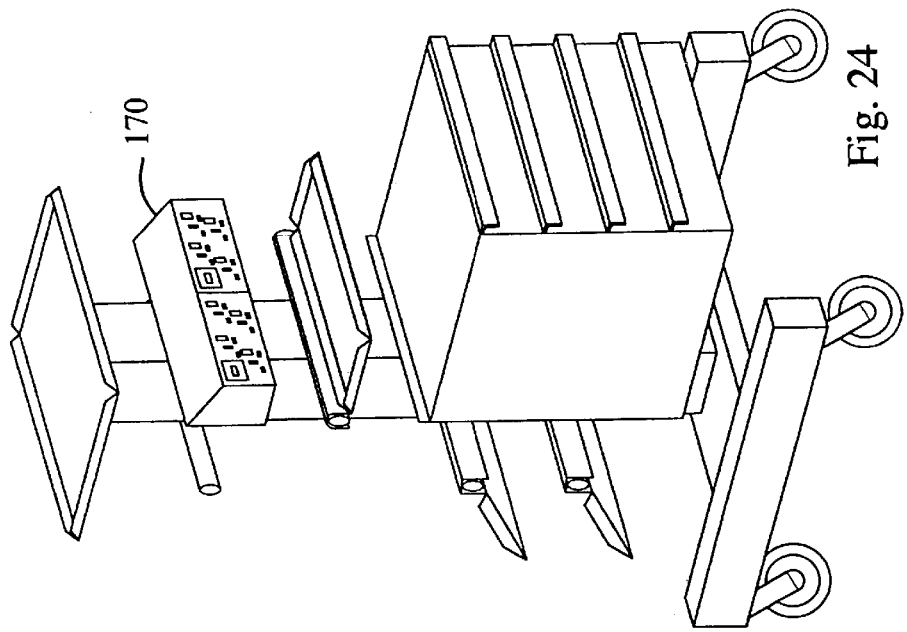
FIG. 24 is a perspective view of the standard mobile according to FIG. 23, seen from the opposite side compared to FIG. 23.
Figure 23:
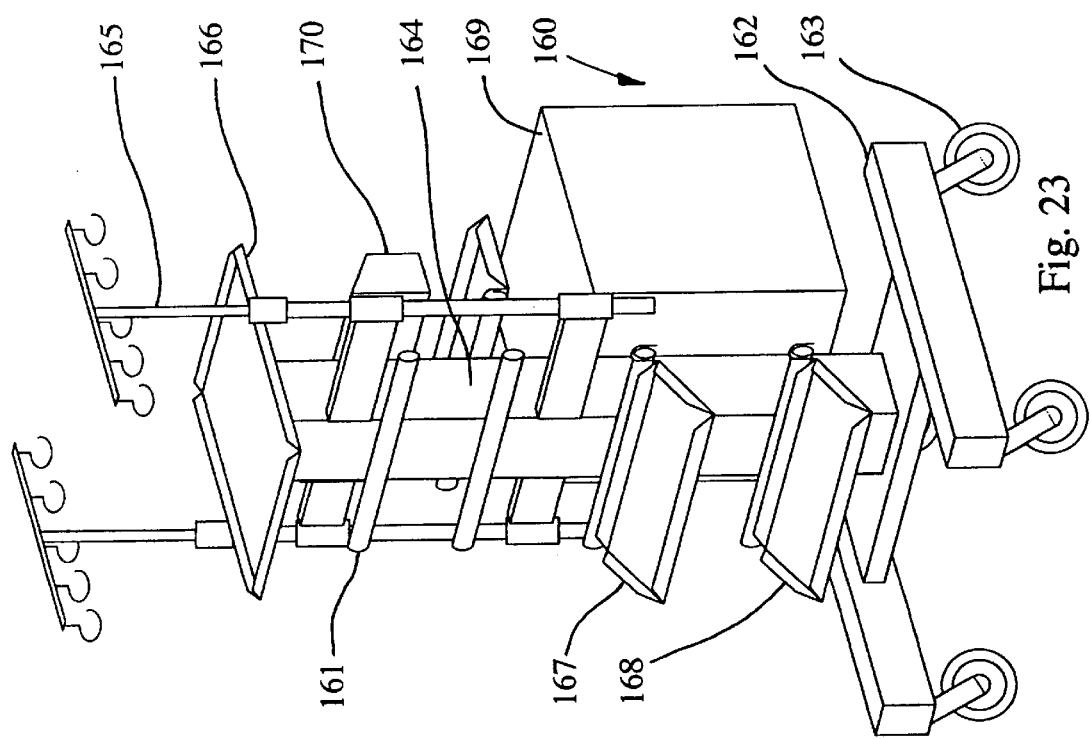
FIG. 23 is a perspective view of a standard mobile according to the invention, seen from the nurse side.

FIGS. 23 and 24 shows a standard mobile according to the invention. The standard mobile 160 is provided with a bottom frame 162 of a more simple structure having four wheels 163 and a single vertical pillar 164. The single pillar is provided with four support rails 161, two infusion bag stands 165, a couple of shelves 166, 167, 168, and a writing table 169. Moreover, an electric panel 170 is provided instead of providing the pillar with electric outlets. This standard mobile 160 can in principle have the same equipment as the CC module 140 described above, but it is smaller and designed for more normal IC cases.

Figure 26:
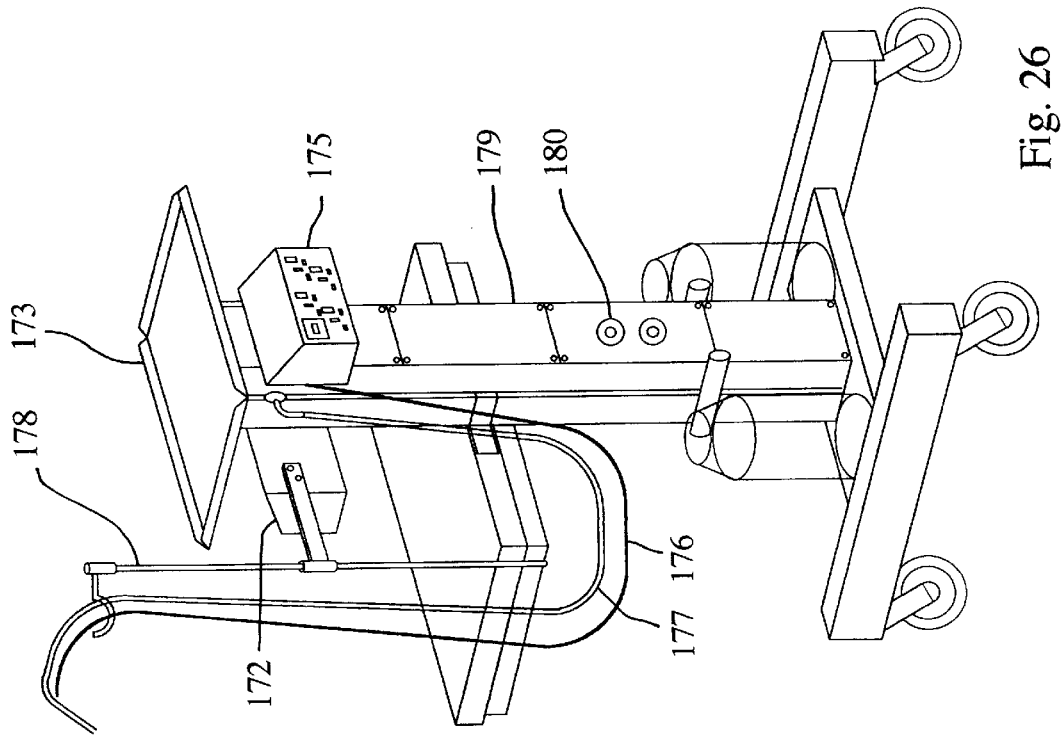
FIG. 26 is a perspective view of the standard mobile according to FIG. 25, seen from the opposite side compared to FIG. 25.
Figure 25:
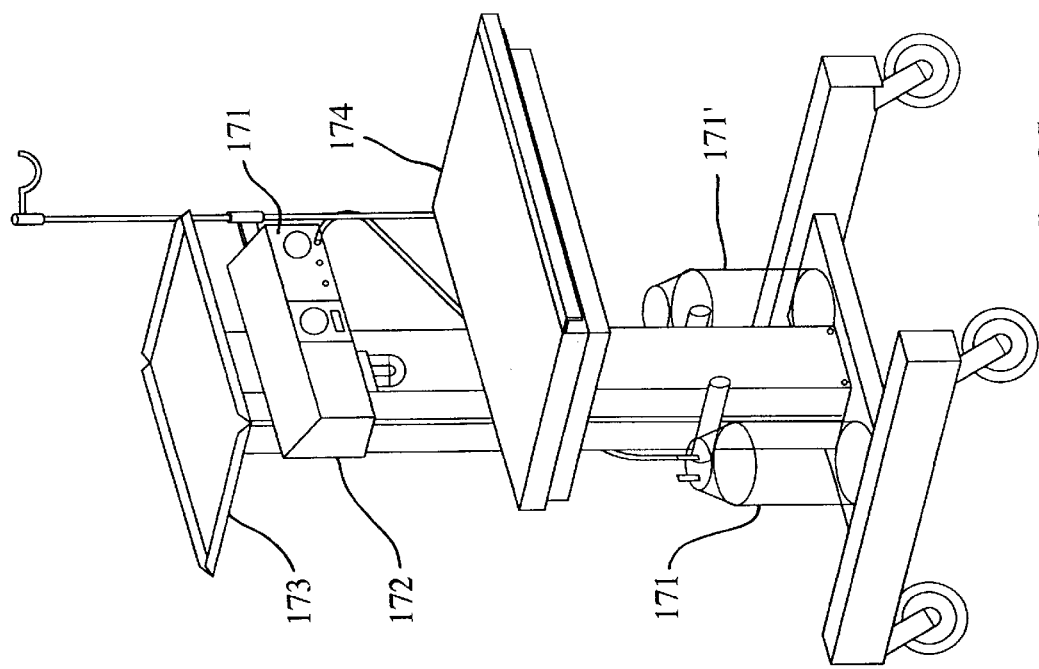
FIG. 25 is a perspective view of the standard mobile according to FIGS. 23 and 24, seen from the patient side and used for another purpose.

As shown in FIGS. 25 and 26, the standard mobile 160 can alternatively be provided as a surgical mobile having one or two individual operation suction units 171, 171' connected to a gas panel 172. Moreover, there is provided a top shelf 173 for any equipment, such as a monitor or a fiber optical light source etc., and a table 174 with a drawer for other equipment, e.g. electrosurgical units. As shown in FIG. 26, there is provided an electric panel 175 with automatic circuit breakers. The gas panel 172 and electric panel 175 are connected to the hospital's central supply via flexible cables 176 and hoses 177 supported by a stand 178 as shown in FIG. 26. The pillar 179 is provided with compressed air outlets 180 for connection to any surgical tools. The upper shelf 173 is pivotable with compressed air outlets 180 for connection to any surgical tools. The upper shelf 173 is pivotable for convenient access from all sides.

Such a standard mobile can be used for many purposes within a hospital.

Although several embodiments have been described above with reference to the appended drawings, it is obvious to a skilled person that different modifications can be made to the embodiments shown on the drawings and different combinations can be made without departing from the inventive idea of the invention. Such modifications obvious to a skilled person reading this specification is intended to be within the scope of the invention.

I claim:

1. Supportive structure intended to be attached to a ceiling of a hospital room for supporting hospital equipment, comprising supporting beams (1,2,3,4) and support profiles (22) for supporting the equipment and for forming a space comprising electric connections and gas connections for said equipment, whereby gas ducts (42) are adapted to enter said space and be connected to gas connection outlets for connection to said equipment, wherein electrical wires (43) are adapted to enter the inside of an electric box (44) gas tight, said electrical box arranged in said space and comprising terminals (45) and being gas tight, and wherein hoses (46) are adapted between said equipment and said electric box, said hoses including gas tight connections (47) for said electrical wires (43) between the terminals in said electric box and said equipment in a gas tight manner, said space being covered by a plurality of plates (36,40), at least one of said plates being provided with ventilation holes (49).

2. Structure according to claim 1, further comprising a rectangular framework of beams (1,2,3,4) attached by several vertical beams (5–12) to mounting members (18) attached to the ceiling, said framework being horizontally close to the ceiling, each of said support profiles (22) comprising a horizontal leg (23) for co-operating with an upper surface of a corresponding beam and a vertical leg (25) for co-operating with an inner surface of the corresponding beam; each of said support profiles (22) comprising a connections means (33, 30,31) for connection to and supporting said equipment, said connection means comprising a longitudinal L-beam (33) with a vertical leg to be inserted in a pocket (30) in the support profile (22) and a horizontal leg for co-operating with a flange surface (31) so that said L-beam is supported by said support profile (22), said L-beam being provided with a connection means for connection to said equipment.

3. Structure according to claim 2, wherein said equipment is mounted at a support plate (36) extending over said rectangular framework, the support plate being provided with several holes corresponding to holes in said L-beam so that said support plate can be attached to said L-beam and tightening of screws extending through said holes in the support plate and said holes in said L-beam jamming said flange surface between said support plate and said L-beam.

4. Structure according to claim 2, wherein each of said support profiles (22) further comprises a hook flange (27) for hooking around said beam at the opposite side of said vertical leg.

5. Structure according to claim 4, wherein said support profile (22) comprises a lock profile (35) to be attached to said hook flange (27) and a cover profile (34) below said beam so that said beam is completely surrounded by said support profile, at least along a portion of the length thereof.

6. Structure according to claim 2, wherein said gas connections are non-interchangeable gas connections.

7. An apparatus for intensive care rooms, said apparatus comprising connectors for gas supply and suction, electric power supply and other electric connectors, said apparatus forming a support structure for equipment close to the bed in an intensive care room, said apparatus comprising a rectangular frame with four beams encircling an essentially rectangular space, said frame being supported by a pivotable arm and a bearing in order to extend essentially vertically from the arm and downward and adjacent to the floor of said room, said rectangular space enclosing equipment interleaved from one side or the other and protected by the frame, and said rectangular space being open for allowing sight through the frame for supervision of a patient, an area around the vertical beams being free for service, said rectangular frame comprising two vertical beams interconnected at the top and bottom by horizontal beams, the horizontal beam at the top being pivotally connected to said bearing of the pivotable arm at or adjacent the middle of the horizontal beam, and wherein the rectangular frame is provided with electrical outlets and a gas panel, said electrical outlets being supplied by power supply wires enclosed inside one of said vertical beams, said horizontal beam and said pivotable arm for connection to a central supply and network of the hospital, and said gas panel being supplied by flexible hoses inside one of said vertical beams, said horizontal beam and said pivotable arm for connection to a central gas supply of the hospital, wherein each of said vertical beams (86,87) comprises grooves extending along the beams for attachment of brackets (112) for supporting holders (100) or other equipment.

8. An apparatus according to claim 7, wherein said rectangular frame comprises electronic connections (108) and outlets (107,109) mounted in or at the vertical beams (86, 87).

9. An apparatus according to claim 7, further comprising a gas panel (96) mounted across the vertical beams.

10. An apparatus according to claim 7, further comprising means in at least one of the bearings (83, 84) for improving stability of the rectangular frame.

11. Supportive structure intended to be attached to a ceiling of a hospital room for supporting hospital equipment, comprising supporting beams (1,2,3,4) and support profiles (22) for supporting the equipment and for forming a space comprising electric connections and gas connections for said equipment, whereby gas ducts (42) are adapted to enter said space and be connected to gas connection outlets for connection to said equipment, wherein electrical wires (43) are adapted to enter the inside of an electric box (44) gas tight, said electrical box arranged in said space and comprising terminals (45) and being gas tight, and wherein hoses (46) are adapted between said equipment and said electric box, said hoses including gas tight connections (47) for said electrical wires (43) between the terminals in said electric box and said equipment in a gas tight manner, said structure further comprising a rectangular framework of beams (1,2,3,4) attached by several vertical beams (5–12) to mounting members (18) attached to the ceiling, said framework being horizontally close to the ceiling, each of said support profiles (22) comprising a horizontal leg (23) for cooperating with an upper surface of a corresponding beam and a vertical leg (25) for cooperating with an inner surface of the corresponding beam; each of said support profiles (22) comprising a connection means (33, 30, 31) for connection to and supporting said equipment, said connection means comprising a longitudinal L-beam (33) with a vertical leg to be inserted in a pocket (30) in the support profile (22) and a horizontal leg for cooperating with a flange surface (31) so that said L-beam is supported by said support profile (22), said L-beam being provided with a connection means for connection to said equipment.

12. Structure according to claim 11, wherein said equipment is mounted at a support plate (36) extending over said rectangular framework, the support plate being provided with several holes corresponding to holes in said L-beam so that said support plate can be attached to said L-beam and tightening of screws extending through said holes in the support plate and said holes in said L-beam jamming said flange surface between said support plate and said L-beam.

* * * * *

UNITED STATES PATENT AND TRADEMARK OFFICE
CERTIFICATE OF CORRECTION

PATENT NO. : 6,089,518
DATED : July 18, 2000
INVENTOR(S) : Agne Nilsson

It is certified that error appears in the above-identified patent and that said Letters Patent is hereby corrected as shown below:

<u>Title page,</u>
Item [73], Assignee, "Slovenia" should read -- Singapore --.

Signed and Sealed this

Twelfth Day of October, 2004

JON W. DUDAS
*Director of the United States Patent and Trademark Office*